(12) United States Patent
Cook, Jr.

(10) Patent No.: US 9,932,640 B1
(45) Date of Patent: Apr. 3, 2018

(54) **CLINICAL USE OF AN *ALU* ELEMENT BASED BIOINFORMATICS METHODOLOGY FOR THE DETECTION AND TREATMENT OF CANCER**

(71) Applicant: George Wyndham Cook, Jr., Baton Rouge, LA (US)

(72) Inventor: George Wyndham Cook, Jr., Baton Rouge, LA (US)

( * ) Notice: Subject to any disclaimer, the term of this patent is extended or adjusted under 35 U.S.C. 154(b) by 858 days.

(21) Appl. No.: 14/265,413

(22) Filed: Apr. 30, 2014

Related U.S. Application Data

(63) Continuation-in-part of application No. 14/154,303, filed on Jan. 14, 2014.

(60) Provisional application No. 61/818,830, filed on May 2, 2013.

(51) Int. Cl.
*G06F 19/10* (2011.01)
*C12Q 1/68* (2018.01)

(52) U.S. Cl.
CPC ...... *C12Q 1/6886* (2013.01); *C12Q 2600/118* (2013.01); *C12Q 2600/156* (2013.01); *G06F 19/10* (2013.01)

(58) Field of Classification Search
CPC .......... G06F 19/19; G06F 19/20; G06F 19/10
See application file for complete search history.

(56) References Cited

PUBLICATIONS

L. Jorde and S. Wooding, Genetic variation, classification and 'race', Nov. 2004, Nature Genetics, 528-533, 36-11.
A. Iafrate, L. Feuk, et al., Detection of large scale variation in the human genome, Sep. 2004, Nature Genetics, 949-951,36-9.
J. Sebat, B. Lakshmi, et al., Large-Scale Copy Number Polymorphism in the Human Genome, Jul. 2004, Science, 525-528, 305.
D. Wheeler, M. Srinivasan, et al., The complete genome of an individual by massively parallel DNA sequencing, Apr. 2008, Nature, 872-877, 452.
G. Abecasis, A. Auton, et al., An integrated map of genetic variation from 1,092 human genomes, Nov. 2012, Nature, 56-65; 491.
R. Redon, S. Ishikawa, et al., Global variation in copy number in the human genome, Nov. 2006, Nature,444-454, 444.

(Continued)

*Primary Examiner* — Mary K Zeman

(57) ABSTRACT

The present invention relates generally to the field of human genetics. More specifically, this invention relates to the clinical application of a bioinformatics methodology described in patent application Ser. No. 14/154,303 for the early detection of cancer. Said clinical application relates to obtaining the genome sequence from an individual's healthy tissue and comparing it to the DNA sequence obtained from that same individual's body tissues, wastes and/or fluids. Said method inspects the DNA sequence obtained from body tissues, wastes and/or fluids for the presence of DNA damage at bioinformatically predicted genetically unstable loci within cancer-linked regions of the patients healthy DNA. The identification of DNA damage within a predicted locus is considered to be evidence of cancer. Said method then uses the unique signature of any damaged DNA sequence which has occurred at predicted unstable cancer-linked loci to construct patient-specific cancer biomarker(s). These biomarkers can be used for monitoring the progression of cancer and for treatment of the cancer in a patient.

1 Claim, 4 Drawing Sheets

(56) References Cited

PUBLICATIONS

R. Mills, W. Pittard, et al., Natural genetic variation caused by small insertions and deletions in the human genome, Apr. 2011, Genome Research, 830-839, 21.

C. Bruder, A. Piotrowski, Phenotypically Concordant and Discordant Monozygotic Twins Display Different DNA Copy-Number-Variation Profiles, Mar. 2008, The American Journal of Human Genetics, 763-771, 82.

J. Visvader, Cells of origin in cancer, Nature, 314-322, 469.

L. Yates and P. Campbell, Evolution of the cancer genome, Nov. 2012, Nature Reviews Genetics, 795-806, 13-11.

L. Garraway and E. Lander, Lessons from the Cancer Genome, Mar. 2013, Cell, 17-37,153.

C. Greenman and P. Stevens, Patterns of somatic mutation in human cancer genomes, Mar. 2007, Nature, 153-158, 446-7132.

B. Vogelstein, N. Papadopoulos, et al., Cancer Genome Landscapes, Mar. 2013, Science, 1546-1558, 339.

M. McConnell, M. Lindberg, Mosaic Copy Number Variation in Human Neurons, Nov. 2013, 632-637, 342.

L. MacConaill and L. Garraway, Clinical Implications of the Cancer Genome, Dec. 2010, 5219-5228, 28-35.

S. Forbes, N. Bindal, et al., COSMIC: mining complete cancer genomes in the Catalogue of Somatic Mutations in Cancer, Oct. 2010, Nucleic Acids Research, D945-D950, 39.

J. Harrow, A. Frankish, et al., GENCODE: The reference human annotation for the ENCODE Project, Sep. 2012, Genome Research, 22, 1760-1774.

M. Stratton, Exploring the Genomes of Cancer Cells: Progress and Promise, Mar. 2011, Science, 1553-1558, 331.

D. Hanahan and R. Weinberg, Hallmarks of Cancer: The Next Generation, Mar. 2011, Cell, 646-674, 144.

M. Lawrence, P. Stojanov, et al., Discovery and saturation analysis of cancer genes across 21 tumor types, Jan. 2014, Nature, 495-503, 505.

S. Shah, A. Roth, et al., The clonal and mutational evolution spectrum of primary triple-negative breast cancers, Jun. 2012, Nature, 395-399, 486.

E. Hayden, The $1,000 genome, Nature, Mar. 2014, 294-295, 507.

S. Leon, B. Shapiro, et al., Free DNA in the Serum of Cancer Patients and the Effect of Therapy, Mar. 1977, Cancer Research, 646-650, 37.

M. Jung, S. Klotzk, et al., Changes in Concentration of DNA in Serum and Plasma during Storage of Blood Samples, Jun. 2003, Clinical Chemistry, 1029-1029, 49-6.

K. Chan, P. Jiang, et al., Cancer Genome Sequencing in Plasma: Detection of Tumor-Associated Copy Number Aberrations, Single-Nucleotide Variants, and Tumoral Heterogenicity by Massively Parallel Sequencing, Clinical Chemistry, 211-224, 59-1.

A. Newman, S. Bratman, et al., An utrasensitive method for quantitating circulating tumor DNA with broad patient coverage, Apr. 2014, Jan. 2013, Nature Medicine (advanced online publication), 1-9, 20-4.

S. Dawson, D. Tsiu, et al., Analysis of Circulating Tumor DNA to Monitor Metastatic Breast Cancer, Mar. 2013, The New England Journal of Medicine, 1199-1209, 368-13.

C. Bettegowda, M. Sausen, et al., Detection of Circulating Tumor DNA in Early- and Late-Stage Human Malignancies, Feb. 2014, Science Translational Medicine, 1-21, 6-224.

A. Albuquerque, I. Kubisch, et al., Prognostic and Predictive value of circulating tumor cell analysis in colorectal cancer patients, Nov. 2012, Journal of Translational Medicine, 1-6, 10-222.

C. Kahlert et al., Identification of Double Stranded DNA Spanning all Chromosomes with Mutated KRAS and p53 DNA in the Serum Exosomes of Patients, with Pancreatic Cancer, Jan. 2014, The Journal of Biological Cancer, 289-7, 3869-3875.

D. Hanahan and R. Weinberg, The Hallmarks of Cancer, Jan. 2000, Cell, 100, 57-70.

S. Jahr, H. Hentz, et al., DNA Fragments in the Blood Plasma of Cancer Patients: Quantitations and Evidence for Their Origin from Apoptotic, and Necrotic Cells, Feb. 2001, Cancer Research, 61, 1659-1665.

G. Cook, M. Konkel, et al., Jun. 2013, A Comparison of 100 Human Genes Using an Alu Element-Based Instability Model, Jun. 2013, PLOS ONE, 8-6, 1-14.

M. Duca, P. Vekhoff, et al., The triple helix: 50 years later, the outcome, Aug. 2008, Nucleic Acids Research, 36-16, 5123-5138.

D. Jantz and J. Berg, Probing the DNA Binding-Affinity and Specificity of Designed Zing Finger Proteins, Mar. 2010, Biophysical Journal, 98, 852-860.

Example of a Multiplex Primer Design for Identifying Possible DNA Damage

CLINICAL USE OF AN *ALU* ELEMENT BASED BIOINFORMATICS METHODOLOGY FOR THE DETECTION AND TREATMENT OF CANCER

CROSS REFERENCE TO RELATED APPLICATIONS

This application is a continuation-in-part of non-provisional application Ser. No. 14/154,303, filed on 14 Jan. 2014, the entire contents of which is hereby expressly incorporated by reference herein. This invention also claims the benefit of provisional application Ser. No. 61/818,830 filed 2 May 2013.

BACKGROUND OF THE INVENTION

1. Field of Invention

The field of the present invention generally relates to the field of human genetics and applies to a medical benefit derived from the bioinformatic prediction of DNA damage at a cancer-linked locus of instability that can be used as a biomarker for the early detection and subsequent treatment of cancer.

2. Description of the Related Art

Our knowledge of the human genome is undergoing a revolution. Within this decade it was putatively believed that the genomes within humans were 99.9% identical {1}—(Jorde and Wooding 2004). This belief in a very high level of human genome homology was shattered by the identification of vast stretches of DNA that vary in copy number (diploid copy number=2) between individuals {2-3}—(Iafrate et al. 2004; Sebat et al. 2004). It has recently been shown that extensive variation exists between the genomes of healthy individuals {4-5}—(Wheeler et al. 2008; Abecasis et al. 2012). Changes in human-to-human genomic copy number most often takes the form of deletions or duplications. This new form of variation is now described by the term, copy number variation (CNV). Human-to-human genome heterogeneity is now thought to be as high as 12% {6}—(Redon et al. 2006). Further undermining the traditional view of high human-to-human genome homology is the finding that almost 2 million insertions and deletions exist between the genomes of 79 humans {7}—(Mills et al. 2011). Even identical twins have been shown to be not genetically identical {8}—(Bruder et al. 2008).

Cancer is now routinely described as a disease of the genome {9-11}—(Visvader 2011; Yates and Campbell 2012; Garraway and Lander 2013). Sequencing of cancer genomes has shown that approximately 80% of mutations are unrelated to the cancer phenotype and are referred to as passenger mutations {12}—(Greenman 2007). The preponderance of passenger mutations in human cancer is further supported by the observation that a colorectal tumor from a 90-year old patient typically contains approximately twice as many mutations as a similar tumor in a 45-year old patient {13}—(Vogelstein et al. 2013). Single-cell sequencing of 110 individual human frontal cortex neurons reveals 45 of these neurons have one or more unique megabase-sized deletion or duplications. These neurons were obtained from three deceased individuals between the ages of 20 and 26 {14}—(McConnell et al. 2013).

Within the background of passenger mutations, the repeated occurrence of commonly mutated genes in multiple tumor genomes permits cancer-linked genes to be statistically distinguished from passenger mutations. This repeated occurrence permits identification of the cancer-linked genes as targets for further examination as potential drivers of cancer. These driver mutations represent the subset of mutations which collectively impart the phenotype of unregulated growth to cancer cells. {15-16}—(Macconaill and Garraway 2010; Forbes et al. 2011). The ENCODE project has estimated that there are 20,687 protein coding genes in the human genome {17}—(Harrow et al, 2012). However, the number of cancer-linked genes within the human genome has been estimated to be between 83 and 400 {16, 18, 13}—(Forbes et al 2011; Stratton 2011; Vogelstein et al. 2013). Consequently, less than 2% of human genes have been linked to cancer.

The collective mutations within the DNA of a pre-cancer cell slowly accumulate over time, often over a period of decades. The impact of accumulated mutational damage among the subset of cancer-linked genes results in the eventual expression of the cancer cell phenotype {18}—(Stratton 2011). A putative minimum of eight to ten mutated cancer-linked genes are necessary to acquire the cancer phenotype {19-20}—(Hanahan and Weinberg 2012; Lawrence et al. 2014). However, only a small fraction of cancer-linked genes are mutated in over 20% of cancers in a given cancer type, with most cancer-linked genes mutated at frequencies of 2%-20% {20}—(Lawrence et al. 2014). Consequently, it is possible to have two cancers of the same phenotype and yet be quite different in their respective sets of driver mutations. Indeed, cases of triple-negative breast cancer have been observed that have totally different sets of mutated cancer-linked genes. In other words, cases of triple-negative breast cancers have been found that do not share even a single mutated cancer-linked gene in common {21}—(Shah et al. 2012). Adding to the complexity of the genetic mechanisms that drive cancer is a recent evaluation of high-throughput sequencing technology. This evaluation found high-throughput sequencing technology was only able to identify 159 of 251 (63%) driver mutations in cancers identified by Sanger sequencing in the evaluation of a tumor genome {13}—(Vogelstein 2013).

Two recent developments have accelerated the advancement in personalized cancer treatment. The first development is the advent of the high-throughput sequencing, also known as next-generation sequencing. This technology has dramatically reduced the cost of sequencing a human genome. Over the past six years, with next-generation technology, the cost of sequencing a human genome has dropped from approximately $10 million to a few thousand dollars {22}—(Hayden 2014). The second development is advancement of an earlier discovery that circulating free DNA (cfDNA) is present in the bloodstream of humans and is present in elevated concentrations in cancer patients {23}—(Leon et al. 1977). The concentration of cfDNA has been measured at approximately 1,200 genome equivalents per ml of blood plasma {24}—(Jung et al. 2003). The concentration of circulating free tumor DNA (ctDNA) adds to the normal concentration of cfDNA in the blood. The concentration of ctDNA in the blood has also been shown to be a strong function of tumor size. Larger tumors can actually contribute more ctDNA to the bloodstream than the amount of DNA normally present as non-tumor cfDNA in the blood {25-26}—(Chan et al. 2013; Newman et al. 2014). Sampling a cancer patient's blood for tumor-specific DNA is commonly referred to as a liquid biopsy {27-28}—(Dawson et al. 2013; Bettegowda et al. 2013). Other sources of tumor DNA in the bloodstream of cancer patients can also be present in the form of circulation tumor cells and DNA excreted from tumor cells within exosomes {29-30}—(de Albuquerque et al. 2012; Kahlert et al. 2014).

One of the limits of current cancer identification technology is that a tumor must often grow to the level of a health challenging phenotype before it is detected. By combining next-generation sequencing with ctDNA monitoring, it is now possible to determine if the surgical removal of a tumor has been successful. It is also possible to determine if the cancer has returned following surgery. This is accomplished by first sequencing the DNA of the tumor, second, identifying tumor specific loci within the tumor DNA sequence and third, conducting follow-up monitoring for the presence and concentration of the tumor DNA in the patient's bloodstream {28}—(Bettegowda et al. 2014). Therefore, the identification of tumor specific loci within the tumor genome has become a valuable cancer biomarker. Unfortunately, until the genome of a tumor is sequenced, it is not currently possible to know which of the many cancer-linked genes, if any, actually contain driver mutations.

Early detection of cancer is the preeminent goal of cancer diagnostics. However, many therapies for cancer are designed for treating the mutational phenotypes of cancer such as training the immune system to kill cells with a mutated surface protein or tailoring drugs to inhibit kinases involved in aberrant signaling pathways. Estimating individual cancer risks are limited to estimates based upon family cancer histories, various lifestyle habits (such as smoking), inherited single nucleotide variations that have shown to correlate with cancer susceptibility, etc. None of these current methodologies identify a likely locus for a gateway mutation—the initiating mutation for a potential tumor cell. Furthermore, the National Cancer Institute estimates that only 5-10% of cancers are inherited. Consequently, the predictive value of history-based methods for estimating cancer risk is limited.

A causative model of genome instability is needed that will permit the development of a method that is capable of predicting a likely locus of cancer-linked genome instability prior to the occurrence of DNA damage. A methodology for predicting instability in cancer-linked regions of healthy DNA sequence prior to DNA damage could prove invaluable. Such technology would be transformative to cancer diagnostics (Professor Sir Michael R. Stratton, "The Genomes of Cancer Cells", Jean Shanks lecture, Annual General Meeting of the Academy of Medical Sciences, Nov. 21, 2013). The ability to anticipate cancer-linked mutations would permit monitoring for, and early identification of, damaged DNA leaking out from very early cancers. The ability to monitor healthy individuals for the first occurrence of cancer-linked mutations would be far superior to the current state-of-the-art techniques. Current techniques are only capable of monitoring cancer after a tumor has been identified.

The attainment of early cancer detection technology will require a fundamental understanding of the mechanisms that generate human genome instability. If the mechanisms of genomic instability can be modeled, genome damage can be anticipated prior to tumor detection. Cancer treatment often begins following tumor detection, which often occurs decades after the first cancer mutations have occurred {18}—(Stratton 2011). The ability to anticipate the first cancer-linked mutations prior to their formation would be a transformational technological achievement. Such an achievement would be a significant advancement in cancer diagnosis and treatment.

SUMMARY OF THE INVENTION

The present invention relates generally to the field of human genetics and more specifically to the field of early cancer detection. Specifically the present invention is a continuation of non-provisional application Ser. No. 14/154, 303, and relates to the clinical use of this application's described bioinformatics methodology, the entire contents of which is hereby expressly incorporated by reference herein.

More specifically, the present invention relates to methods and materials that are associated with the aforementioned bioinformatics methodology. These methods and materials are used to examine predicted regions of high genome instability within or near cancer-linked regions of an individual's genome for DNA damage. The present invention further relates to the monitoring for DNA damage which has occurred in biopsies of an individual's body tissues, wastes and/or fluids. This DNA damage may occur within predicted regions of high genome instability at cancer-linked loci. DNA damage is identified by comparing the DNA sequence of the aforementioned biopsies to the DNA sequence obtained from healthy tissue from the same individual. This cancer-linked DNA damage may be indicative of tumor formation.

The present invention also relates to the use of the unique signature of damaged DNA sequence within bioinformatically predicted cancer-linked loci as a cancer biomarker. The invention further relates to the use of these cancer-linked biomarkers for the diagnosis and prognosis of human cancers. Finally, the invention relates to the use of the aforementioned cancer biomarkers for isolating the location of cancers, for monitoring of cancer progression and for evaluating the efficacy of surgery, drug treatment and other cancer therapies.

DETAILED DESCRIPTION OF THE INVENTION

Figure 1:
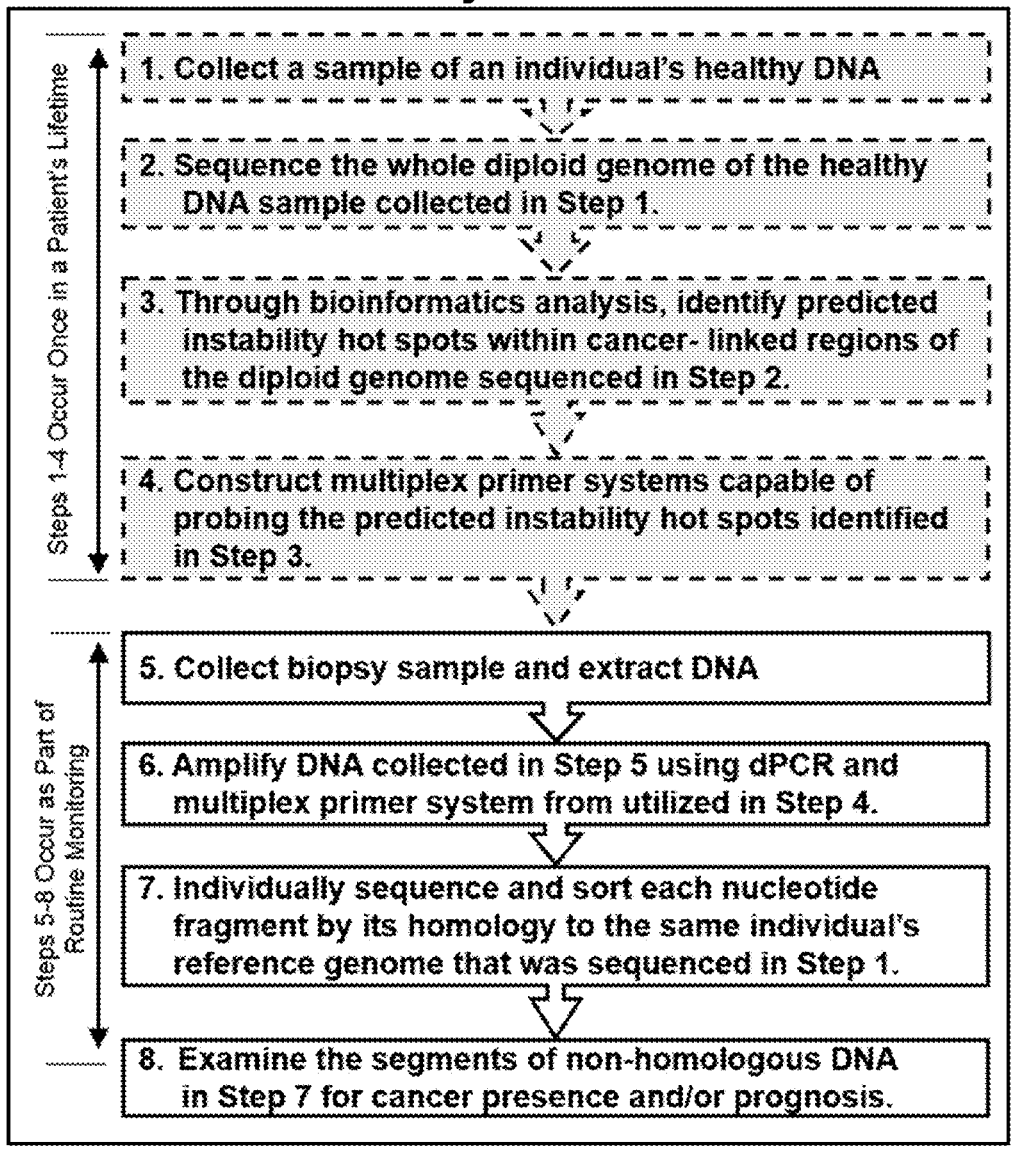
FIG. 1 illustrates the step by step methodology for the detection of tumor DNA described in Example 1.

The present invention relates generally to the field of human genetics and more specifically to the field of early cancer detection. More specifically, the present invention is a continuation of non-provisional application Ser. No. 14/154,303, the entire contents of which is hereby expressly incorporated by reference herein. This invention, also claims the benefit of provisional application Ser. No. 61/818,830 filed 2 May 2013.

This invention further relates to the clinical application of the bioinformatics technology described in the aforementioned non-provisional application Ser. No. 14/154,303. This invention provides a methodology for obtaining the genome sequence from an individual's healthy tissue and comparing it to the DNA sequence obtained from the same individual's body tissues, wastes and/or fluids. This methodology examines the DNA sequence obtained from an individual body tissues, wastes and/or fluids for the presence of DNA damage at bioinformatically predicted genetically unstable loci within cancer-linked regions, as compared to the genome sequence obtained from the individual's healthy tissue.

It should be noted that the sequencing of the DNA obtained from healthy tissue is only required once in the lifetime of the individual. However, the subsequent sequencing of DNA from body tissues, wastes and/or fluids would occur on a routine basis such as the sequencing of DNA taken from blood samples as part of a routine annual physical exam, or as part of a sampling regime recommended by a physician. The detection of alterations in the DNA sequence within the cancer-linked loci of body tissues, wastes and/or fluids is considered herein to be an early indicator of the potential presence of cancer.

The present invention provides for the monitoring of a putatively cancer-free individual's body tissues, wastes and/or fluids for the early detection of cancer. This monitoring is achieved by the bioinformatics-guided detection of cancer-linked mutations. An embodiment of this portion of the invention is provided in Example 1 and is briefly outlined in FIG. 1.

The present invention also uses an individual's unique nucleotide signature associated with cancer-linked damaged DNA sequence to construct cancer-specific probes. These probes can be designed to bind to the cancer-specific nucleotide sequence on and even within a tumor. These probes can be constructed from complementary RNA, from synthetic groups of complementary zinc fingers or other DNA binding molecules for identifying the location of cancer. An embodiment of this portion of the invention is provided in Example 2.

The present invention also provides for the use of the aforementioned unique nucleotide biomarker for monitoring of cancer progression. An embodiment of this portion of the invention is provided in Example 3.

The present invention also provides for evaluating the efficacy of surgery, and various drug treatments and other cancer therapies. This evaluation is made possible by monitoring the concentration of the aforementioned cancer-specific nucleotide biomarker in the patient's body tissues, wastes and/or fluids. This evaluation can be conducted before during and after cancer treatment. An embodiment of this portion of the invention is provided in Example 4.

The aforementioned cancer-specific probes can also be used as a delivery agents for cancer chemotoxins and/or drugs to a tumor. This could be accomplished by direct covalent attachment, or by chemical tethering via a linker molecule of these agents to the cancer-specific probes. An embodiment of this portion of the invention is provided in Example 5.

Cancer is a "disease of the genome" {9-11}—(Visvader 2011, Yates and Campbell 2012; Garraway and Lander, 2013). One of the hallmarks of cancer is genomic instability {19}—(Hanahan and Weinberg, 2012). As the understanding of the fundamentals of cancer has developed, the number of recognized hallmarks of cancer has increased. Over the past 15 years, the number of recognized hallmarks associated with cancer have increased from six, to eight to ten {31, 19-20}—(Hanahan and Weinberg, 2000; Hanahan and Weinberg, 2012; Lawrence 2014). The acquisition of these hallmarks is thought to be the result of the accumulation of genomic damage imparted by the inherent instability of the cancer genome. This damage may occur over a period of decades {18}—(Stratton 2011) Detection of these cancer-specific mutations can provide a biomarkers which can then be used for diagnosis, monitoring and treatment of that specific cancer {25, 27, 20, 26}—(Chan et al. 2013; Dawson et al. 2013; Kahlert et al. 2014; Newman et al. 2014).

Early detection of cancer can be the difference between life or death for a cancer patient. Even the most advanced cancer treatments require prior development of some physical or health-related phenotype for cancer to be detected. With current technology, samples from a solid tumor, body waste and/or fluid for a patient exhibiting a physical or health-related phenotype can currently be sequenced to identify the presence of cancer-linked genetic biomarkers. However, the use of this invention's genetic biomarkers would provide for the much earlier detection of cancer. The current delay in waiting for development of a physical or health-related phenotype for cancer detection can result in a period of months or years of delay in cancer detection {18}—(Stratton, 2011). This delay in diagnosis provides time for the cancer to acquire additional mutations and develop a more aggressive phenotype which can require a more aggressive treatment regime.

It is recognized that false positives may occur with this methodology, because not all cancer-linked mutations may result in the eventual development of neoplastic tissue into cancer. However, the presence of a potential false positive can be validated by subsequent testing and routine patient monitoring. For instance, when the presence of a potential biomarker is first detected at the lower detection limit of a given analysis, routine monitoring would detect any increase in the biomarkers concentration. This bioinformatically-guided technology thus adds valuable time for cancer treatment that is not presently available with current technology.

Tumor DNA was first reported in the blood of cancer patients in 1977 {23}—(Leon et al. 1977). Since this initial discovery, tumor DNA has been found to be present in three forms in the bloodstream; as circulating fragments of tumor DNA (ctDNA), within circulating tumor cells and within excreted exosomes from tumor cells {25, 28, 30}—(Chan et al. 2013; Bettegowda et al. 2014; Kahlert et al. 2014). Circulating tumor cells are absent from over 50% of cancers that contain ctDNA {28}—(Bettegowda et al. 2014). Limited data is available in the literature for the presence of tumor DNA contained within exosomes. Most published reports of the use of blood as a liquid biopsy for early cancer detection have most recently focused on the use of ctDNA {27-28}—(Dawson et al. 2013; Bettegowda et al. 2013).

The bloodstream typically contains the cellular equivalent of approximately 1,200 cells of fragmented DNA per ml {24}—(Jung et al. 2003). This normal (non-cancer related) DNA is hereafter referred to as circulating free DNA (cfDNA). The necrosis and apoptosis of cancer cells adds ctDNA to the normal base load of cfDNA {32}—(Jahr et al. 2001). It has recently been discovered that tumor size correlates strongly with the concentration of ctDNA as a fraction of the total DNA in the blood stream {25-26}—

Figure 2:
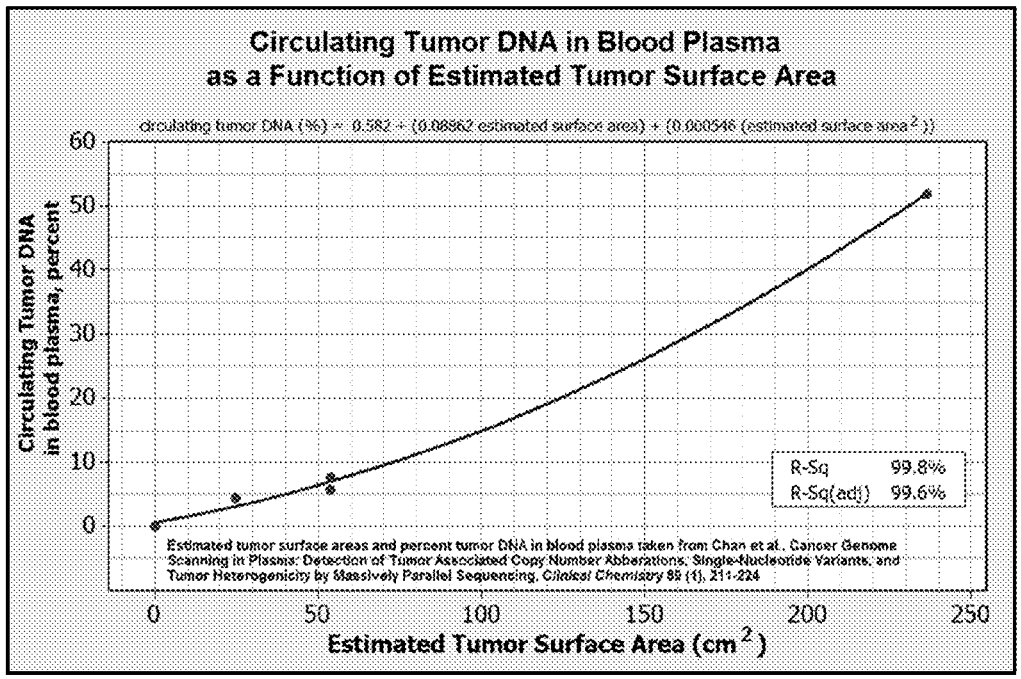
FIG. 2 illustrates a regression analysis of the percent of circulating tumor DNA (ctDNA) in the blood plasma as a function of the estimated tumor surface area (see also Table 2 in Example 1).
Figure 3:
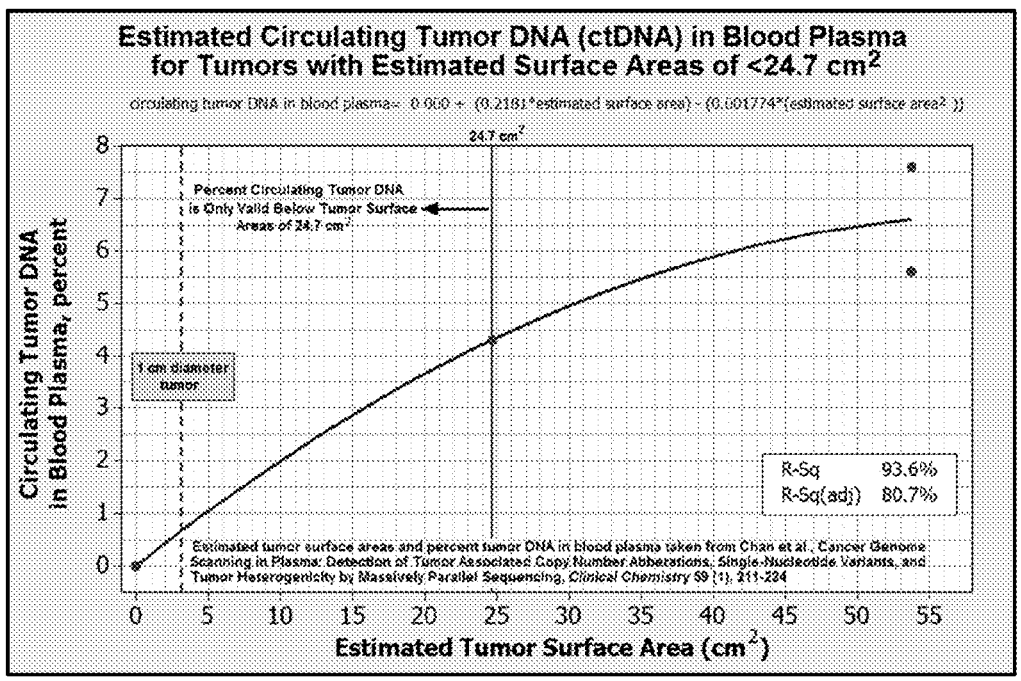
FIG. 3 illustrates a regression analysis of the percent of circulating tumor DNA (ctDNA) in blood plasma as a function of the estimated tumor surface area. Note that this curve passes through zero surface area and zero ctDNA concentration and only applies for tumors which have an estimated surface area of less than 24.7 $cm^2$ (see also Table 2 in Example 1).

(Chan et al. 2013; Newman et al. 2014). Examples of how the percent ctDNA in the blood plasma can vary as a function of tumor size are illustrated in FIGS. 2 and 3.

Current technology for the early detection of cancer has two significant limitations. The first limitation is that the cancer cells within a common tumor have been shown to be genetically heterogeneous and thus often share different sets of driver mutations that confer the characteristic hallmarks of cancer. This heterogenicity results from the inherent instability of cancer cells. As cancer progresses, the progeny of cancer cells are constantly mutating {13}—(Vogelstein et al. 2013). The only certain common mutation within a tumor (or tumor system in the case of metastic cancer) is the gateway mutation which is the first cancer-linked mutation. The gate mutation imparts the initial the growth advantage to a tumor cell. Current technology has no way of predicting genome instability. Current science can only speculate as to which mutation among the population of mutated cancer-linked genes is the common or gateway mutation {18}— (Stratton 2011). Therefore, without knowledge of the gateway mutation, it is possible for a subset of cancer cells to develop from the original tumor and escape detection.

Deletion prone cancer-linked genes have an estimated average length of 77.0 kbp {33}—(Cook et al. 2013). Assuming a population of 400 cancer-linked linked genes, there is approximately 30.8 million base pairs of cancer-linked sequence in the haploid human genome {18}— (Stratton 2011). Consequently, the landscape of the diploid cancer-linked regions of the human genome collectively spans over 60 million base pairs of DNA sequence. Identification of a pre-cancerous driver mutations with current technology within this expanse of DNA is akin to looking for a needle in a haystack. This invention provides for a bioinformatically-guided evaluation of the various cancer-linked sequences. The not only reduces the search area for potential DNA damage to a given gene, but also points to where within the span of a given gene, genomic damage is likely to occur. This approach reduces the search area for possible cancer driver mutations to less than 50,000 base pairs of sequence, which is a 1,000× reduction in the likely area for a deletion. The ability to focus on a small region of the human genome brings the very early detection of cancer within the reach of current technology (see Example 1). This reduced search area also makes routine monitoring for the presence of cancer economically feasible.

Current treatments for cancer often attempt to kill cancer cells by targeting cancer cell hallmarks. For instance killing cancer cells with chemo-toxic drugs targets the cancer hallmark of higher metabolism. Tuning the immune system to kill cancer cells by targeting a mutated surface protein addresses the cancer hallmark of tissue invasion. Administration of drugs to inhibit kinases that are involved in aberrant signaling pathways may target the cancer hallmark of high cell division. The present invention differs from these aforementioned cancer treatments. This invention approaches cancer from its etiology by creating biomarkers for the genetic mutations that are the root cause of the cancer.

Current treatments for cancer target the symptoms of cancer. These treatments often attempt to kill cancer cells with techniques such as chemo-toxic drugs; destroy the cancer cells with the immune system; or halt the cancer with drugs tailored to inhibit kinases involved in aberrant signaling pathways. The present invention does not treat the aforementioned techniques for treating symptoms of cancer, but approaches cancer from its etiology. It addresses the root cause of the genomic instability that is characteristic of cancer cells.

The primary goal in this invention is to detect the unique DNA sequence that separates a given cancer from the healthy DNA from which it originates. Because all cancers are the result of DNA damage, the knowledge of the DNA sequence across the DNA damage of the predicted locus for the gateway mutation serves as a unique biomarker for that cancer. The ability to identify the DNA sequence across the breakpoint of cancer-linked DNA damage not only provides evidence of a potential cancer, but also provides the critical DNA sequence that is uniquely specific to that cancer. Detecting this DNA sequence is the preeminent goal of cancer diagnostics. Example 1 provides a method for identifying this cancer biomarker. Examples 2-5 will demonstrate that awareness of this biomarker can create new diagnostic and therapeutic options for the treatment of a specific cancer.

A. DEFINITIONS

The terms "3'" and "5'" refer to the upstream and downstream directions from a genomic reference point, respectively.

The term "Alu element" refers to a repetitive section of DNA in the human genome, typically 275-300 base pairs in length and is classified as a short interspersed DNA element (SINE). Over one million Alu elements are present in the human genome and account for approximately ten percent of its sequence.

The term "Alu Landscape" refers to the set of Alu elements that reside within and flank a cancer-linked region of an individual's genome.

The term "biomarker" refers to any element related to a tumor that is specifically informative about that tumor's prognosis, behavior or its response to therapy.

The term "breakpoint" refers to the sequence breakpoint relative to an original DNA sequence, following the repair of one or more double-strand breaks.

The term "bp" refers to a genetic distance or length of a DNA sequence in base pairs.

The term "Copy Number Variation" refers to a change in the number of copies of a segment or segments of DNA in a genome of interest as compared to a reference genome. Because of the diploid nature of human DNA, most regions of human DNA are present as two copies. Therefore, copy number variation for most human regions of DNA would be either greater than or less than two.

The term "cfDNA" refers to circulating free DNA in human blood.

The term "ctDNA" refers to circulating tumor DNA found in the blood of cancer patients.

The term "depth of sequencing" is a term that relates to next generation sequencing and refers to the total number of times the average nucleotide base is sequenced. This can be calculated by dividing the total number of bases that are sequenced by the number of bases in the original DNA sequence being amplified.

The term "diploid" refers to two complete copies of the nuclear genome. Most human cells are diploid.

The term "driver mutation" refers to the subset of mutations within a tumor cell that confer a growth advantage.

The term "emulsion PCR" refers to the technique of conducting PCR in an oil/water emulsion. This provides a means for amplifying a single fragment of DNA by the creation of very small droplets for conducting separate aqueous PCR reactions, which use a single and different fragment of DNA as the template strand. This technique can be used in conjunction with deep sequencing to detect small fractions of DNA where genomic variation is present. It is ideally suited for detection of the presence of low concentrations of tumor DNA that may be mixed with the normal DNA found in the bloodstream.

The term "ENCODE project" refers to a research program established for the purpose of identifying all functional elements within the human genome and is referred to as the Encyclopedia Of DNA Elements.

The term "gateway mutation" refers to the initiating disruption to the DNA sequence in a cancer cell, which ultimately results in the cell's development into a cancer phenotype. It should be noted that this initiating disruption may not confer any growth advantage to the cancer cell, but may only impart genome instability that will eventually result in damage to genes that control cellular proliferation.

The term "germline mutation" refers to a mutation which occurs in the genome of germ cells, and can therefore be inherited by offspring.

The term "hallmark mutation" refers to a cancer-linked mutation which contributes to one or more of the characteristic attributes recognized in the cancer phenotype.

The term "haploid" refers to a single copy of a nuclear genome.

The term "indel" refers to a DNA sequence that is present in one genome, but is absent from another. With only two genomes with which to compare, it cannot be known whether the extra DNA sequence resulted from an insertion in one genome or a deletion in the other. This conundrum of the origin of this sequence is therefore expressed as a conjugation of the two words insertion and deletion.

The term "kbp" refers to 1,000 base pairs of nucleotide sequence.

The term "megabase" refers to one million base pairs of DNA sequence.

The term "multiplex" refers to a technique in which several regions of a genome can be amplified together. In the context of this application, this multiplex technique refers to the amplification of the DNA within a region of high instability which was detected within a cancer-linked region of the DNA.

The term "neoplasm" refers to a mass of tissue that is the result of a higher rate of cell division within the mass of tissue than the rate of cell division present in the surrounding cells. This tissue mass often exhibits some differentiation from the surrounding tissue.

The term "next generation sequencing" is a general term that refers to several different methods of DNA sequencing that have been developed after the original Sanger method of DNA sequencing. These newer methods of DNA sequencing are much faster and can be conducted at much lower cost than the original Sanger sequencing.

The term "orthologous" refers to a common gene that is present in two different species.

The term "passenger mutation" refers to a mutation in a cancer cell that conveys little or no fitness to that cell. These mutations are also referred to as "innocent bystander" mutations. These mutation can either be the direct result of cancer cell instability or DNA damage that occurred during normal cell metabolism, during or prior to the cell acquiring the driver mutation.

The term "PCR" refers to the "polymerase chain reaction" which is a biochemical method for amplifying a fragment of DNA. The length of the DNA that is amplified is typically less than 1,000 base pairs in length, but in some cases can be a few thousand base pairs in length.

The term "plasma" refers to the liquid portion of blood that does not contain red blood cells, white blood cells (leukocytes) or platelets.

The term "Sanger Sequencing" refers to a method of DNA sequencing that was discovered in 1977 and was used in the Human Genome Project. While more expensive than "next-generation" high throughput sequencing, it is still in use and is considered the gold standard for sequencing accuracy.

The term "serum" refers to blood plasma with the blood clotting fraction removed.

The term "somatic" refers to the body.

B. EXAMPLES

The described embodiments in Examples 1-5 below represent the preferred embodiments of the present invention. However, it is to be understood that those skilled in the art of genetics can modify these various methodologies associated with these embodiments of the invention without departing from its spirit. The examples are intended to be exemplary of the invention.

Example 1

Determination if a Cancer-Linked DNA Sequence is Present in a Blood Sample

Detection of the presence of cancer-linked DNA damage in the DNA of a blood biopsy sample is an indicator of the presence of a neoplasm that may be cancerous or may become cancerous. The general methodology described in this example is summarized in FIG. 1. As would be expected from a methodology capable of very early detection of cancer, false positives will likely occur at some frequency. Whether the detection of the presence of a cancer-linked mutation is actually an indicator of cancer can be validated by subsequent testing and routine patient monitoring. For instance, if the presence of a potential biomarker is detected, but this biomarker is only present at the lower detection limit of a given analysis, routine monitoring can be performed to detect any increase in the biomarkers concentration. This bioinformatically-guided technology thus adds valuable time for cancer treatment that is not presently available with current technology.

Example 1 describes a general methodology for the potential detection of a cancer-linked DNA sequence in an individual's bloodstream. As noted in the body of this application, the bloodstream has been shown to be a reservoir for tumor-derived DNA. The amount of tumor DNA that is present has been shown to be a function of tumor size (see FIGS. 2 and 3). Consequently, blood samples can be used as a liquid biopsy for monitoring an individual for the presence of cancer-linked DNA damage. Other sources of potential cancer-linked mutations can also be obtained from biopsies of an individual's body tissues, wastes and/or fluid. This example is intended to be only exemplary as one application of this invention.

A primary goal of this invention is the detection of the sequence breakpoint associated with any cancer-linked DNA damage. Because of its uniqueness to a given cancer, determination of this cancer-linked sequence is the preeminent goal of cancer diagnostics. As will be apparent in Examples 2-5, identification of this damaged DNA sequence opens up many new diagnostic and therapeutic options for a specific cancer. The eight steps outlined in FIG. 1 and described in more detail below, outline the general methodology for identifying the unique sequence that is associated with cancer-linked DNA damage in a blood sample.

Note from FIG. 1 and in the methodology described below, that Steps 1-4 occur once in the lifetime of the individual. Steps 5-8 should occur on a routine basis as part of an annual physical exam or as part of a regime recommended by a physician.

Step 1—Collect the DNA from an individual's healthy tissue.

Step 2—Sequence the diploid genome of the DNA collected in Step 1. The sequence of this original DNA sample will be used as a reference sequence to detect whether DNA damage as compared to a second sample of DNA obtained from a biopsy.

Step 3—Using the bioinformatics methodology claimed in patent application Ser. No. 14/154,303, identify the regions of highest instability within the cancer-linked regions of the diploid genome sequenced in Step 2.

Figure 4:
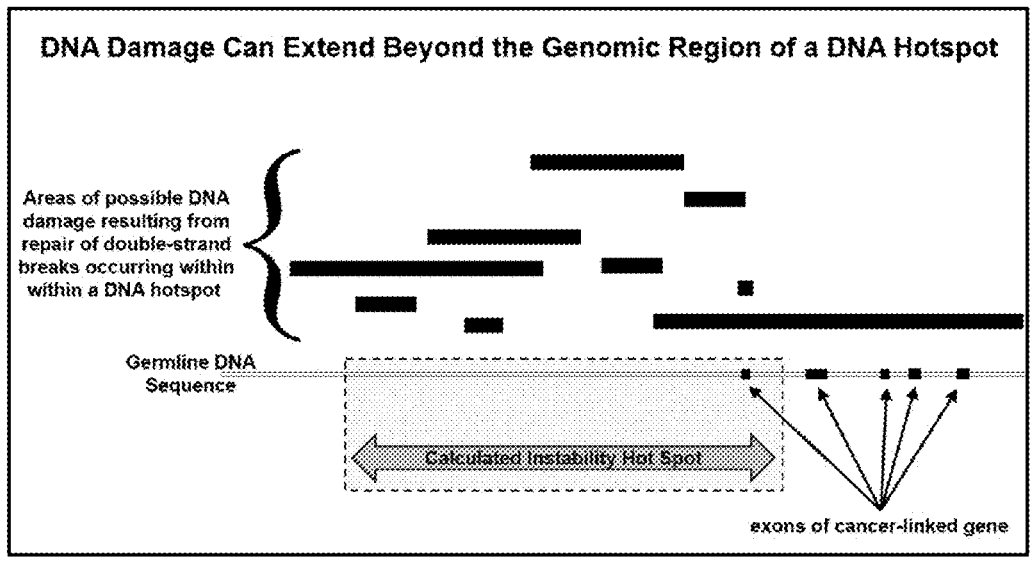
FIG. 4 illustrates how DNA damage can vary in size and can extend beyond a predicted region of genomic instability.

Step 4—Construct a multiplex primer system for the purpose of amplifying the region of DNA which is most likely to encounter the genomic instability with subsequent DNA damage. As FIG. 4 illustrates, determining the location and size of damaged DNA is not an easy task. The calculated region of genome instability is shown in the large shaded double-arrowed line at the middle of the bottom of the figure. Examples of possible DNA damage are shown as black rectangles. Although each of these examples of possible DNA damage originate within the dashed area described by the double-arrowed line, the extent of this damage can be short or long and can extend outside of the region and into the exons of the cancer linked gene at the bottom right of the figure.

Figure 5:
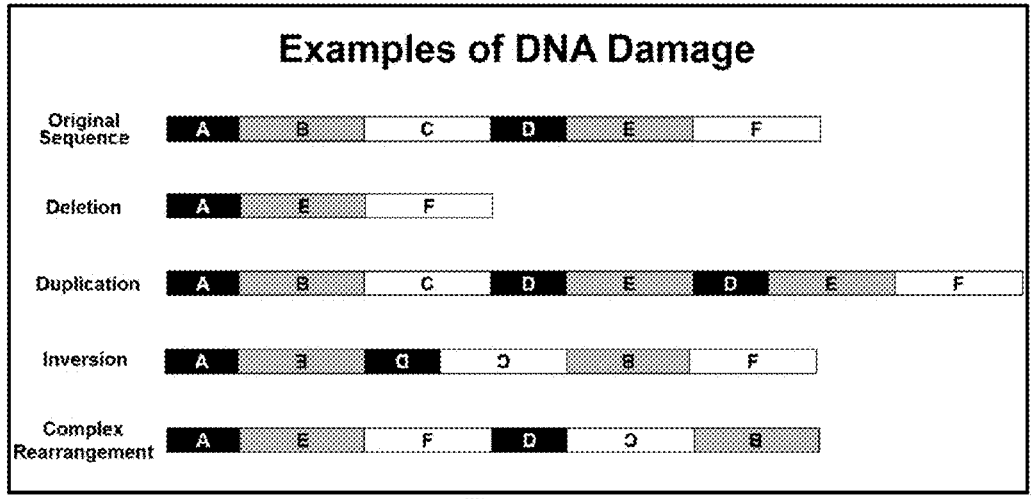
FIG. 5 illustrates five different forms of DNA damage.

FIG. 5 provides an example of four different kinds of DNA damage that might occur at a cancer-linked locus. The top DNA sequence consists of regions A, B, C, D, E and F that make up an original DNA sequence. Immediately below this original sequence is an example of a deletion which removes regions B-D. The central sequence is an example of duplication which duplicates regions D-E in the original sequence. The next to last sequence is an example of an inversion which inverts regions B-E in the original sequence. Finally, the bottom sequence is an example of a complex rearrangement. A multiplex primer system must be capable of detecting these various types of DNA damage.

Figure 6:
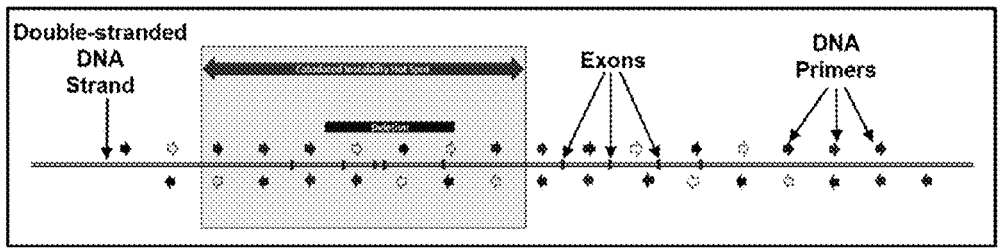
FIG. 6 provides an example of a multiplex primer system designed for identifying cancer-specific breakpoints of DNA damage associated with a region of predicted high genomic instability.

Although the genomic instability of a given cancer-linked region of the genome can be predicted based on a specific Alu element landscape, the extent of any resultant DNA damage is unknown. A multiplex primer system such as the example illustrated in FIG. 6 must be designed for each predicted unstable locus. Consequently a multiplex primer system such as the example illustrated in FIG. 6 must be designed for each predicted unstable locus. In this example, this region of the genome will be amplified from the circulating DNA in the blood and will ultimately be deeply sequenced (Step 7, below). However, because the multiplex region is small compared to the length of the human genome, the cost of this sequencing is far less than the cost of sequencing an entire genome.

Figure 7:
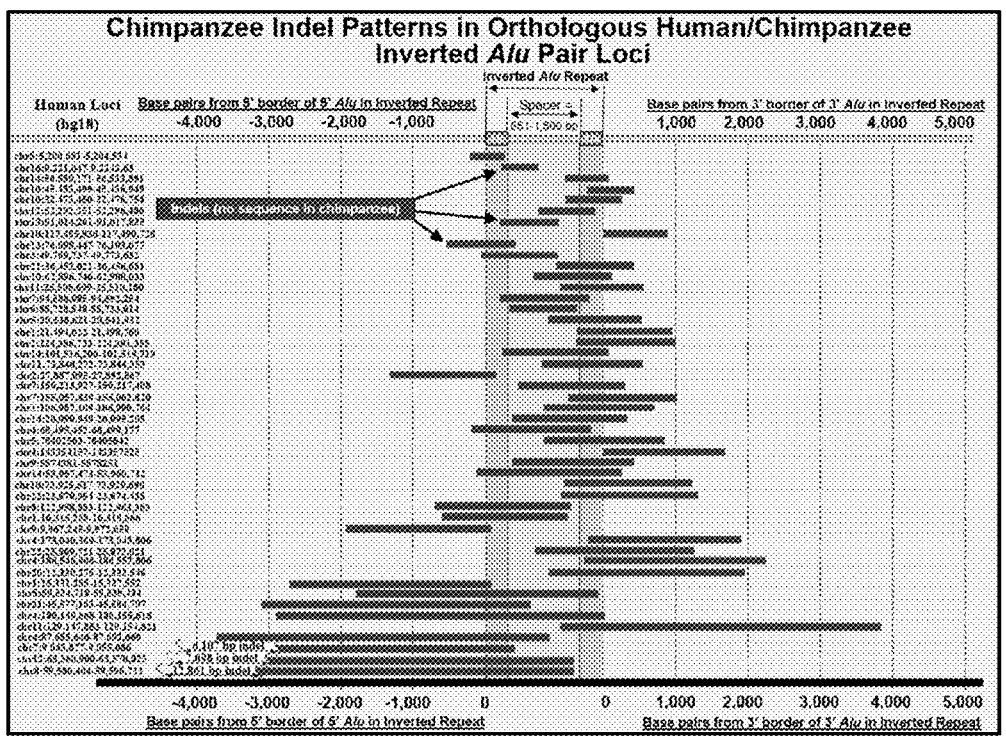
FIG. 7 illustrates the deletion patterns across inverted Alu pairs in orthologous human and chimpanzee DNA sequences which have not undergone deletions.

FIG. 7 provides 48 examples of orthologous regions of inverted Alu pairs that are common between the human and chimpanzee genomes. The inverted Alu pair loci shown in this figure have undergone deletions in the chimpanzee genome only. The size of these deletions provide an estimate of the size of the region that might be damaged by inverted Alu pair instability. The bottom three loci in this figure show the largest deletions that have occurred in this analysis. These three largest deletion sizes are as follows; 6,107 base pairs, 7,698 base pairs and 12,861 base pairs. The sizes of 18 human health related Alu element deletions that have been recently reported are provided in Table 1. Only one of these deletions is greater than 50,000 bp (56,600 bp) and 13 of 18 (72%) of these deletions are less than 10,000 bp.

The human Alu element-mediated deletions in Table 1 are in reasonable agreement with the observed chimpanzee deletions shown in FIG. 7. Consequently, a 50,000 bp window of DNA damage inspection provides a reasonable estimate of what will be required for detection of cancer-linked DNA damage. However, the size of this window is not intended to be limiting, but only exemplary for this present invention.

TABLE 1

Recent Reports (2012-2013) of Alu Element Mediated Deletions[1]

| First Author | Journal | Year of Publication | Deletion No. | Deletion Size, bp | Disease Gene |
|---|---|---|---|---|---|
| Vaughn, CP | GC&C[2] | 2013 | 1 | ~1,500 | PMS2 |
|  |  |  | 2 | ~2,000 | PMS2 |
|  |  |  | 3 | ~2,000 | PMS2 |
| Duraturo, F | BRI[3] | 2013 | 1 | 9,655 | MSH2 |
| Pezzoli, L | Gene | 2012 | 1 | 3,505 | MYBPC3 |
| Pereria, MC | GiM[4] | 2012 | 1 | 1,056 | SPG11 |
|  |  |  | 2 | 1,489 | SPG11 |
|  |  |  | 3 | 8,323 | SPG11 |
|  |  |  | 4 | 2,710 | SPG11 |
| Mahmoudi, H | ED[5] | 2012 | 1 | 12,200 | LPAR6 |
| Jelassi, A | CCA[6] | 2012 | 1 | 12,684 | LDLR |
|  |  |  | 2 | 2,364 | LDLR |
| Silva, AG | BMC Cancer | 2012 | 1 | 36,400 | BRCA1 |
| Eiden-Plach, A. | JSB&MB[7] | 2012 | 1 | 12,100 | StAR |
| Coutinho, MF | JIMD[8] | 2012 | 1 | 897 | GNPTAB |
| Chanavat, V | EJMG[9] | 2012 | 1 | 3,505 | MYBPC3 |
| Bondurand, D | EJMG | 2012 | 1 | 56,600 | SOX10 |
| Barbaro, M | IJGM&PM[10] | 2012 | 1 | 3,381 | CPDX |

[1]References from Cook et al., 2013
[2]Genes, Chromosomes & Cancer
[3]Biomed Research International
[4]Genetics in Medicine
[5]Experimental Dermatology
[6]Clinica Chimica Acta
[7]Journal of Steroid Biochemistry & Molecular Biology
[8]Journal of Inherited Metabolic Disease
[9]European Journal of Medical Genetics
[10]International Journal of Genetic, Molecular and Personalized Medicine Step 5—Collect a 15 ml blood sample from the same individual whose healthy DNA was sequenced in Step 2 and extract the DNA from the blood plasma. Since whole blood is about 55% plasma, approximately 8 mls of plasma can be recovered from the 15 ml blood sample. The concentration of DNA in the blood plasma is approximately 600 cells (1,200 genome equivalents) per ml {24}—(Jung et al. 2003). Therefore, the plasma sample contains the DNA equivalent of approximately 4,800 cells.

Step 6—Amplify the extracted DNA (Step 5) within the cancer-linked regions that have the highest predicted instability (Step 3) with the multiplex DNA system (Step 4).

Step 7—Sequence each fragment of DNA from the multiplex amplification conducted in Step 6. This can be done with emulsion PCR.

Step 8—Using the appropriate software, examine each of the sequenced DNA fragments sequenced in Step 7 for homology to the DNA that was sequenced from healthy tissue in Step 2. The purpose of this examination is to identify any DNA fragments that are homologous to regions of DNA that are normally separated. The presence of such "dual homology" DNA fragments indicates that cancer-related DNA damage is present in the blood stream.

The cost of sequencing a region of DNA from a human blood biopsy is directly related to the cost of sequencing a whole human genome. A typical human genome is sequenced to a depth of 30× with next generation sequencing. Therefore the total base pairs that are normally sequenced in a human genome using next generation sequencing is approximately 189 billion bp (30× coverage× 6.3 billion bp in a diploid human genome=189 billion bp). If the cost of sequencing the blood biopsy DNA is limited to one percent of the cost of whole genome sequencing, the number of bases which could be sequenced in the blood biopsy is 1.89 billion (189 billion bp/100). Assuming that the multiplexed region (Step 6) covers 50,000 base pairs, or 100,000 base pairs for a diploid cell, the depth of coverage over this region of the genome would be 18,900 (1.89 billion bp/100,000 bp) which would provide a depth sequence coverage for the blood biopsy of 18,900×. This depth of coverage is critical for identifying trace amounts of tumor DNA within the blood biopsy. The ability to detect trace amounts of tumor DNA is critical for early cancer detection. The ability to economically sequence DNA from blood biopsies can provide a platform for the widespread availability of early cancer detection.

The size of a potential tumor can be derived from a curve such as the one shown in FIG. 3. If 100 copies of the "split read" DNA fragments are detected from the 18,900× coverage, the cancer DNA concentration in the bloodstream would be approximately 0.5% (100 copies of "split read" DNA/18,900× coverage). Using the curve in FIG. 3, this tumor would have an estimated diameter of slightly less than one centimeter. Also, since the blood sample contains the equivalent of approximately 4,800 cells, an estimated 24 tumor cells would be present in the 8 ml plasma sample (4,800×0.005).

Finally, the ability to sequence the blood biopsy samples of multiple individual's in the same sequencing operation can be achieved by using the technique of "DNA barcoding". DNA barcoding involves ligating a small DNA marker that is specific to an individual patient to the end of the DNA fragment that is being amplified. The incorporation of DNA barcoding with this methodology would allow multiple patients to be examined in a single sequencing run, thus reducing the cost per patient.

DNA barcoding can be coupled with the multiplexing strategy described above. Studies of circulating free DNA in the bloodstream have shown that this DNA is fragmented with typical lengths of 170-180 bp {32, 26}—(Jahr et al. 2003; Newman et al. 2014). If these cfDNA fragment lengths are ligated with strands of barcoded DNA which contain a PCR primer binding site, the reverse primer in the multiplex PCR amplification would then be required to be specific to the predicted region of genomic instability being examined.

As will be apparent to one skilled in the science next-generation sequencing, the various methodologies described in Example 1 can be replaced with alternate techniques for the detection of biopsy DNA containing "split read" homologies. The methodologies used in this example are not intended to be limiting for the present invention, but are only intended to be exemplary.

It is estimated that the amount of DNA in human blood plasma is approximately 1,200 genome equivalents per ml {24}—(Jung et al. 2003). Since most human cells are diploid, this DNA concentration is the equivalent of 1,500 cells per ml of human blood serum. In addition to this base load of circulating DNA in healthy blood, an additional burden of tumor DNA is also present in the blood of cancer patients. Patients with larger tumors exhibit larger concentrations of tumor DNA as a fraction of the total DNA in blood plasma. The first four rows of columns one, three and four of Table 2 illustrate tumor-derived DNA in blood plasma from four patients with hepatocellular carcinoma {25}—(Chan et al. 2013).

The bottom row in Table 2 adds an additional point for zero tumor DNA that would be present in a healthy patient. These five data points permit tumor size to be correlated with the amount of DNA found in a cancer patients blood serum. For purposes of estimation, the equivalent diameter of the tumor is assumed to be ⅔ of its maximum dimension. Using this estimate, the best correlation of the data in Table 2 is equivalent tumor surface area versus percent tumor-derived DNA in the blood. These correlations are shown in FIG. 2 and FIG. 3.

Note that the best fit for the regression curve in FIG. 2 does not pass through zero. The data point for zero tumor DNA at zero tumor surface area was added to this set of data because of the need to detect cancer at its earliest stages. As an example, note the dashed vertical line in FIG. 3 which represents a tumor with a spherical equivalent of 1 cm in diameter (surface area of 3.14 cm$^2$). This regression curve estimates that a tumor of this size would contribute approximately 0.7% of tumor DNA to the total circulating free DNA in the bloodstream. It should be noted that this data was taken from Chan et al. 2013. This study examined tumor DNA concentrations associated with hepatocellular carcinoma. A similar graph is shown in FIG. 3C of Newman et al. 2014. This second graph represents an estimate of tumor size versus circulating tumor DNA concentration for non-small cell lung cancer. Similar graphs can be generated for different cancers which may improve the estimates of tumor size versus circulating tumor DNA concentration. The regression analyses provided in FIGS. 2 and 3 are only exemplary and are not intended to be limiting for the present invention.

TABLE 2

Estimated Tumor Surface Area vs Tumor-Derived DNA in Blood Plasma

| Maximum Dimension of the Tumor[1] | Tumor Surface Area if Spherical at a Diameter of ⅔ of Maximum Dimension | Concentration of Tumor-derived DNA in Blood Plasma | |
|---|---|---|---|
| (cm) | (cm$^2$) | Before Surgery | After Surgery |
| 13.0 | 236.2 | 52.% | 0.9% |
| 6.2 | 53.7 | 7.6% | 2.7% |
| 6.2 | 63.7 | 5.6% | 0.9% |
| 4.2 | 24.7 | 4.3% | 1.4% |
| 0.0 | 0.0 | 0.0% | 0.0% |

[1]Columns 1, 3 and 4 (except for last row) were taken from Chan et al. 2013.

Example 2

Use of the Damaged DNA Sequence at a Bioinformatically Predicted Cancer-Linked Region in an Individual's Genome as a Biomarker for Locating a Tumor RNA has been shown to bind to complementary double-stranded DNA to form a DNA-DNA-RNA triplex helix {34}—(Duca et al. 2010). It has also been shown that engineered zing fingers can be designed to bind to DNA in a sequence specific manner {35}—(Jantz and Berg 2010). Either of these techniques could be used to bind to cancer specific DNA. If these probes were added to the bloodstream, any unbound probes would likely find their way to the surface of the tumor and bind to the DNA leaking from the tumor. If RNA or engineered zing fingers are synthesized which are also radioactively labeled, the tumor could then be located via CT scans or PET-CT scans.

As will be apparent to one skilled in the science of biochemistry, variations of DNA sequence specific binding by other molecules may be possible. The molecules used in this example are not intended to be limiting for the present invention; but are only intended to be exemplary.

Example 3

Use of the Damaged DNA Sequence at a Bioinformatically Predicted Cancer-Linked Region in an Individual's Genome as a Biomarker for Measuring Tumor Progression The sequence of cancer-linked DNA damage gained from Example 1 can be uses as an excellent cancer biomarker for the detection of tumor progression. With this biomarker routine monitoring of the bloodstream for an increase in biomarker concentration can serve as a method for measuring tumor progression.

When the presence of tumor DNA is identified in the bloodstream of a patient, subsequent tumor monitoring would entail repeating Steps 4-8 in Example 1, with one important difference. Step 4 would no longer require the multiplex primer system for identifying cancer linked DNA damage. Since the cancer linked DNA damage has been identified, this step would only require the two primers which would amplify the section of DNA containing the "split read" cancer-linked sequence. This would allow for much deeper sequencing at this location and provide for more accurate analysis of tumor DNA concentration, and thus for more accurate estimates of potential tumor growth.

Example 4

Use of the Damaged DNA Sequence at a Bioinformatically Predicted Cancer-Linked Region as a Biomarker in an Individual's Genome for Measuring the Efficacy of Cancer Surgery, Cancer Drugs and/or Therapies The technique described in Example 3 could be used to monitor the level of circulating tumor DNA in the bloodstream to evaluate the efficacy of surgery, cancer drugs or cancer therapies. The ability to compare tumor DNA concentrations in the bloodstream before during and after treatment can assist the physician in determining the success of a given cancer strategy.

Example 5

Use of the Damaged DNA Sequence at a Bioinformatically Predicted Cancer-Linked Region as a Biomarker for Delivery of Cancer Chemicals and/or Drugs to a Tumor Example 2 describes the construction of cancer-specific probes which could be utilized in the location of a tumor. These probes would bind to the tumor. Tethering of cancer chemotoxins and/or drugs to these probes would permit highly cancer-specific administration of these agents to one or more tumors. This higher cancer specificity could also permit higher concentrations of these same agents to be administered to the tumor site (or sites).

What I claim in my invention is:

1. A method for detecting the presence of cancer in a sample, comprising:
    A) obtaining a reference sample from an individual, and a clinical sample from an individual;
    B) determining a genome sequence data of the reference sample;
    C) Identifying regions of genomic instability in the genome sequence data of the reference sample, comprising at least Alu, SVA, LINE element data, Doomsday-junction data, deletion size frequency distribution, and cancer-linked region data;
    D) constructing multiplex primers to amplify regions of genomic instability as defined in step C;
    E) Performing amplification on the clinical sample using the primers of step D, to amplify regions of genomic instability;
    F) sequencing the amplified material of step E to provide clinical sample genome sequence data;
    G) identifying clustering of LINE, SVA and Alu elements within the reference genome sequence data and within the clinical genome sequence data, wherein a cluster of Alu elements can be interspersed with one or more LINE elements and/or SVA elements; and wherein the adjacent elements within Alu element clusters are separated by up to 100 base pairs; and wherein inverted Alu pairs interact to form a Doomsday junction, a double-strand break generating DNA structure;
    H) categorizing Alu pairs in the reference genome and the clinical genome according to the four possible clustering configurations;
        I. both Alus in the pair reside within the same cluster,
        II. both Alus in the pair reside in different clusters,
        III. only one Alu within the pair resides within a cluster, or
        iv. neither Alu in the pair resides within a cluster;
    I) further categorizing the Alu pairs in the reference and clinical genome by the number of base pairs within the spacer separating the two Alu elements which form the Alu pair;
    J) further categorizing the Alu pairs in the reference and clinical genome by the number of Alus within the spacer separating the two Alus which form the Alu pair;
    K) calculating the imbalances between inverted and direct oriented Alu element pairs within the entire reference and clinical genome according to steps H), I) and J); assigning the appropriate imbalance to each inverted Alu pair within the individual genome that reside within three million base pairs of a cancer-linked region according to step G);
        I. wherein the frequency of inverted and direct Alu element pairs within the reference and clinical genome is expressed in a Alu pair 1:D ratio according to H), I), and J);
        II. wherein the assigned Alu pair 1:D ratio is the estimated stability of a single inverted Alu element pair within the clinical genome;
        III. wherein a single Alu element has a specific likelihood of forming a double-strand break from interacting with each of its 110 adjacent inverted Alu pair neighbors in the 5' direction and from interacting with each of its 110 adjacent inverted Alu pair neighbors in the 3' direction according to step G); and wherein the likelihood of each double-strand break is used to calculate the total instability of the end of each Alu element;
  iv. wherein the stability of each end of each Alu element for a single inverted Alu pair interaction in the individual genome is the fourth root of the assigned Alu pair 1:D ratio according to step K)-ii; and
  v. wherein the composite stability of each Alu element end within three million base pairs of a cancer-linked region is calculated by multiplying all individual inverted Alu end stabilities as described in step K)-iv;
L) calculating the distance in base pairs between the end of each Alu element within three million base pairs of a cancer-linked region of the clinical genome according to step K);
M) constructing a deletion size probability distribution which describes the probability that a deletion of a given size or larger that will not result from a double-strand break according to step K) using a human genome deletion size frequency distribution;
N) determining the individual stability of the cancer-linked region as related to a single Alu end by multiplying the composite stability of each Alu element end according to step K)-vi by the likelihood that the double strand break will not create a deletion large enough to extend into the cancer-linked region of the genome according to step M);
O) determining the composite stability of the cancer-linked region by multiplying the products of each individual stability for each respective Alu end within three million base pairs of the cancer-linked region according to step N);
P) determining an individual's susceptibility to cancer by comparing the composite stability of a cancer-linked region according to step O) for the clinical genome to the composite stabilities calculated for that same cancer-linked region for a group of individuals that have developed cancer as a result of genome damage to that same region of the genome; and wherein the lower the stability, the greater the susceptibility to cancer;
Q) detecting the presence of damaged DNA within the cancer-linked region of the clinical genome sequence data by sequencing the amplified sample of step E) at the cancer-linked regions identified in step P);
wherein the presence of damaged DNA within the cancer-linked regions identified in step P in the clinical sample is indicative of the presence of cancer.

* * * * *